(12) United States Patent
Ishikura et al.

(10) Patent No.: US 7,268,234 B2
(45) Date of Patent: Sep. 11, 2007

(54) METHOD FOR SULFONATION OF 1,2-BENZISOXAZOLE-3-ACETIC ACID

(75) Inventors: Tsutomu Ishikura, Suzuka (JP); Nobuhiko Horiuchi, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 11/531,364

(22) Filed: Sep. 13, 2006

(65) Prior Publication Data
US 2007/0066830 A1 Mar. 22, 2007

Related U.S. Application Data

(60) Provisional application No. 60/717,207, filed on Sep. 16, 2005.

(51) Int. Cl.
*C07D 261/20* (2006.01)
(52) U.S. Cl. .................................................. 548/241
(58) Field of Classification Search ................ 548/241
See application file for complete search history.

(56) References Cited

U.S. PATENT DOCUMENTS

| 4,172,896 | A | 10/1979 | Uno et al. |
| 6,841,683 | B2 | 1/2005 | Mendelovici et al. |
| 6,900,333 | B2 | 5/2005 | Ueno et al. |
| 6,936,720 | B2 | 8/2005 | Mendelovici et al. |
| 2003/0144527 | A1 | 7/2003 | Nidam et al. |
| 2006/0009644 | A1 | 1/2006 | Naddaka et al. |
| 2006/0014814 | A1 | 1/2006 | Naddaka et al. |
| 2006/0084814 | A1 | 4/2006 | Siva Kumar et al. |

FOREIGN PATENT DOCUMENTS

| JP | 53-77057 A | 7/1978 |
| JP | 54-163823 A | 12/1979 |
| WO | WO 2005/044808 A1 | 5/2005 |

OTHER PUBLICATIONS

Masanao Shimizu et al., "Research and development of zonisamide, a new type of antiepileptic drug," Yakugaku Zasshi, vol. 116, No. 7, pp. 533-547 (1996), with partial English translation.

Hitoshi Uno et al., "Studies of 3-substituted 1,2-benzisoxazole drivatives. 6. synthesis of 3-(sulfamoylmethyl)-1,2-benzisoxazole derivatives and their anticonvulsant activities," Journal of Medicinal Chemistry, vol. 22, No. 2, pp. 180-183 (1979).

S. Patai and Z. Rappoport, "The chemistry of sulphonic acids, esters and their derivatives," pp. 354-355 (1991), John Willy & Sons.

Hitoshi Uno et al., "Studies on 3-substituted 1,2-benzisoxazole derivatives. V. electrophilic substituions of 1,2-benzisoxazole-3-acetic acid," Chem. Pharm. Bull., vol. 26, No. 11, pp. 3498-3503 (1978).

*Primary Examiner*—Kamal A. Saeed
*Assistant Examiner*—Karen Cheng
(74) *Attorney, Agent, or Firm*—Fitch Even Tabin & Flannery

(57) ABSTRACT

An efficient method for the preparation of 1,2-benzisoxazole-3-methanesulfonic acid involves a reaction of 1,2-benzisoxazole-3-acetic acid in toluene with chlorosulfonic acid optionally mixed with an inert solvent in the presence of a particular Lewis base (ester or a nitrile).

8 Claims, No Drawings

US 7,268,234 B2

METHOD FOR SULFONATION OF 1,2-BENZISOXAZOLE-3-ACETIC ACID

CROSS REFERENCE TO RELATED APPLICATIONS

This U.S. application claims the priority benefit of U.S. Provisional Application No. 60/717,207, filed Sep. 16, 2005, the complete disclosure of which is incorporated herein by reference.

FIELD OF THE INVENTION

The present invention relates to a method for the selective sulfonation of 1,2-benzisoxazole-3-acetic acid in toluene with chlorosulfonic acid. Specifically, the present invention relates to an efficient method of manufacturing 1,2-benzisoxazole-3-methanesulfonic acid comprising reacting 1,2-benzisoxazole-3-acetic acid in toluene with chlorosulfonic acid in the presence of a particular Lewis base other than dioxane. The invention further relates to a novel one-pot method of manufacturing 1,2-benzisoxazole-3-methanesulfonamide.

BACKGROUND OF THE INVENTION 1,2-Benzisoxazole-3-methanesulfonic acid obtained by the sulfonation reaction of 1,2-benzisoxazole-3-acetic acid with chlorosulfonic acid is an intermediate of 1,2-benzisoxazole-3-methanesulfonamide (zonisamide). Zonisamide is useful as an anti-epileptic medicine.

JP-A-53-77057 and Yakugakuzasshi, 116, 533-547 (1996) disclose a process for the preparation of 1,2-benzisoxazole-3-methanesulfonic acid which is produced from a reaction of chlorosulfonic acid and 1,2-benzisoxazole-3-acetic acid in the presence of dioxane in ethylene chloride (1,2-dichloroethane) or dichloromethane.

U.S. Pat. No. 6,841,683, in experiment number TN 2414, and US2003/0144527A1, in experiment number 4, disclose an example in which 1,2-benzisoxazole-3-acetic acid and chlorosulfonic acid are reacted in toluene, and in the reaction mixture there are 63.5%, 3% and 32% of the sodium salt of 1,2-benzisoxazole-3-methanesulfonic acid, the disulfonated benzisoxazole derivative that is a by-product and a starting material (1,2-benzisoxazole-3-acetic acid) respectively. However, U.S. Pat. No. 6,841,683 and US2003/0144527A1 apparently do not disclose or describe the isolation yield and purity of 1,2-benzisoxazole-3-methanesulfonic acid.

U.S. Pat. No. 4,172,896, JP-A-53-77057, JP-A-54-163823 and J. Med. Chem., 22, 180 (1979) disclose a process for the preparation of 1,2-benzisoxazole-3-methanesulfonamide which is produced by a method comprising a step of reacting sodium 1,2-benzisoxazole-3-methanesulfonate isolated as an solid form with phosphorus oxychloride (phosphoryl chloride), and followed by reacting with ammonia gas in ethyl acetate. Using dry ammonia gas is disclosed, for instance, in U.S. Pat. No. 4,172,896 and JP-A-53-77057.

U.S. Pat. No. 6,936,720 discloses a process for the preparation of 1,2-benzisoxazole-3-methanesulfonamide which is produced by a method comprising a step of reacting sodium 1,2-benzisoxazole-3-methanesulfonate with $SOCl_2$/DMF in toluene, and followed by reacting with ammonia gas.

U.S. Pat. No. 6,900,333 discloses a process for the preparation of 1,2-dichlorethane free crystals of 1,2-benzisoxazole-3-methanesulfonamide that is manufactured using 1,2-dichlorethane as a solvent.

While sulfonation of 1,2-benzisoxazole-acetic acid is known to proceed with chlorosulfonic acid and dioxane, it is desirable to avoid the use of dioxane.

Conducting the sulfonation of 1,2-benzisoxazole-3-acetic acid directly with chlorosulfonic acid serving as both a solvent and the sulfonating agent has been reported in Chem. Pharm. Bull., 26, 3498-3503 (1978). The reaction is, however, reported to be quite non-selective and substantial amounts of an undesired di-sulfonated by-product are reportedly produced.

The present inventors turned their attention to toluene as a solvent and concentrated on a method for producing 1,2-benzisoxazole-3-methanesulfonamide from 1,2-benzisoxazole-3-acetic acid as a starting material in a one-pot reaction that does not require isolating any intermediates. Advantages to using toluene as a solvent in such a manufacturing process include 1) reducing usage of a relatively toxic halogenated hydrocarbon, such as 1,2-dichloroethane, 2) ready removal of water from. toluene by azeotropic distillation, which water is from an aqueous sodium hydroxide solution that is used in the manufacturing process, and 3) stability (chemical inertness) to chemical agents such as sodium hydroxide, phosphorus oxychloride and ammonia.

However, it is known that an aromatic compound such as toluene reacts with chlorosulfonic acid easily to yield sulfonic acid derivatives, as seen for example, from S. Patai and Z. Rappoport, The chemistry of sulfonic acids, esters and their derivatives, pages 354-355, 1991, John Wiley & Sons. Consequently, when chlorosulfonic acid was actually added into a mixture of toluene and 1,2-benzisoxazole-3-acetic acid, and the mixture was allowed to react, it was found that sulfonation reaction products of toluene with chlorosulfonic acid and 1,2-benzisoxazole-3-methanesulfonic acid were formed. The aforesaid reaction mixture contained 44% of sulfonation by-product(s), 25% of the desired sulfonation reaction product, and 29% starting material (1,2-benzisoxazole-3-acetic acid) as reported in Reference Example 5 herein. Thus, a simple method such as heating the mixture of 1,2-benzisoxazole-3-acetic acid and toluene with an addition of chlorosulfonic acid is non-selective and can result in the simultaneous sulfonation of toluene, and it is not easy to produce 1,2-benzisoxazole-3-methanesulfonic acid effectively.

In addition, JP-A-53-77057 discloses that dioxane is used as a Lewis base in a sulfonation reaction of 1,2-benzisoxazole-3-acetic acid, but it does not disclose a Lewis base other than dioxane, and especially a Lewis base having low toxicity is apparently not disclosed.

There remains a need for a facile method(s) that is selective to the desired intermediate(s) that are useful in the synthesis of zonisamide, with a sufficiently high yield, and to a facile method for making zonisamide in high purity that avoids the use of dioxane and preferably does not require isolation of any solid intermediates.

SUMMARY OF THE INVENTION

The present inventors conducted extensive studies directed towards a useful manufacturing process of 1,2-benzisoxazole-3-methanesulfonamide, especially an efficient process for preparing 1,2-benzisoxazole-3-methanesulfonic acid comprising a reaction of chlorosulfonic acid and 1,2-benzisoxazole-3-acetic acid in toluene. As a result, the present inventors discovered that 1,2-benzisoxazole-3-methanesulfonic acid is obtained in good yield by sulfonation of 1,2-benzisoxazole-3-acetic acid with chlorosulfonic acid while in toluene in the presence of a particular Lewis base, such as an ester or a nitrile, other than dioxane. It was further discovered that by diluting chlorosulfonic acid with an inert solvent (e.g., chlorinated solvent) and using the diluted chlorosulfonic acid, the above sulfonation reaction can proceed in a higher yield.

In an aspect of the present invention, 1,2-benzisoxazole-3-methanesulfonic acid is obtainable via a sulfonation method that is selective to the desired product and the desired product is substantially free of undesired derivatives and by-products, all without the use of dioxane.

In another aspect of the present invention, the zonisamide is obtainable without the use of dioxane and preferably without isolation of solid reaction intermediates, in a one-pot method.

An aspect of the present invention relates to a method of manufacturing 1,2-benzisoxazole-3-methanesulfonic acid by reacting 1,2-benzisoxazole-3-acetic acid with chlorosulfonic acid, which comprises adding chlorosulfonic acid, optionally mixed with an inert solvent, to a mixture of 1,2-benzisoxazole-3-acetic acid, toluene and a Lewis base, such as an ester or a nitrile, and heating the mixture.

Another aspect of the present invention relates to a method of manufacturing an alkali metal salt of 1,2-benzisoxazole-3-methanesulfonic acid, which comprises adding chlorosulfonic acid, optionally mixed with an inert solvent, to a mixture of 1,2-benzisoxazole-3-acetic acid, toluene and a Lewis base, such as an ester or a nitrile, heating the mixture, and isolating precipitated crystals after adding aqueous alkali metal hydroxide to the reaction mixture.

A further aspect of the present invention relates to a one-pot method of manufacturing 1,2-benzisoxazole-3-methanesulfonamide, which comprises a process including adding chlorosulfonic acid optionally mixed with an inert solvent to a mixture of 1,2-benzisoxazole-3-acetic acid, toluene and a Lewis base, such as an ester or a nitrile, to yield 1,2-benzisoxazole-3-methanesulfonic acid.

These objects and other objects and advantages of the present invention will be understood from the following description by a person skilled in the art.

DETAILED DESCRIPTION OF INVENTION

In its various aspects, the present invention concerns the manufacture of 1,2-benzisoxazole-3-methanesulfonic acid, an alkali metal salt of 1,2-benzisoxazole-3-methanesulfonic acid and 1,2-benzoxazole-3-methanesulfonamide (also known as zonisamide).

In one aspect, the present invention relates to a method of manufacturing 1,2-benzisoxazole-3-methanesulfonic acid by reacting 1,2-benzisoxazole-3-acetic acid with chlorosulfonic acid, which comprises:

adding chlorosulfonic acid, optionally mixed with an inert solvent, to a mixture of 1,2-benzisoxazole-3-acetic acid, toluene and a Lewis base selected from the group consisting of a $C_{2-5}$ saturated aliphatic mono-carboxylic acid $C_{1-4}$ alkyl ester, a benzoic acid $C_{1-4}$ alkyl ester, a $C_{1-4}$ alkyl cyanide and benzonitrile; and heating the mixture.

In an aspect of the present invention for making 1,2-benzisoxazole-3-methanesulfonic acid, the Lewis base is a $C_{2-5}$ saturated aliphatic mono-carboxylic acid $C_{1-4}$ alkyl ester.

In an aspect of the present invention for making 1,2-benzisoxazole-3-methanesulfonic acid, the Lewis base is a $C_{2-5}$ saturated aliphatic mono-carboxylic acid ethyl ester.

In an aspect of the present invention for making 1,2-benzisoxazole-3-methanesulfonic acid, the Lewis base is ethyl acetate or isobutyric acid ethyl ester.

In an aspect of the present invention for making 1,2-benzisoxazole-3-methanesulfonic acid, the inert solvent is dichloromethane, chloroform, or 1,2-dichroloethane.

Another aspect of the present invention relates to manufacturing alkali metal salt(s) of 1,2-benzisoxazole-3-methanesulfonic acid, which comprises:

adding chlorosulfonic acid, optionally mixed with an inert solvent, to a mixture of 1,2-benzisoxazole-3-acetic acid, toluene and a Lewis base selected from the group consisting of a $C_{2-5}$ saturated aliphatic mono-carboxylic acid $C_{1-4}$ alkyl ester, a benzoic acid $C_{1-6}$ alkyl ester, a $C_{1-4}$ alkyl cyanide and benzonitrile;

heating the mixture; and isolating precipitated crystals after adding aqueous alkali metal hydroxide to the reaction mixture.

In an aspect of the present invention for manufacturing alkali metal salt(s) of 1,2-benzisoxazole-3-methanesulfonic acid, the Lewis base is a $C_{2-5}$ saturated aliphatic mono-carboxylic acid acid $C_{1-4}$ alkyl ester.

In an aspect of the present invention for manufacturing alkali metal salt(s) of 1,2-benzisoxazole-3-methanesulfonic acid, the Lewis base is a $C_{2-5}$ saturated aliphatic mono-carboxylic acid ethyl ester.

In an aspect of the present invention for manufacturing alkali metal salts(s) of 1,2-benzisoxazole-3-methanesulfonic acid, the Lewis base is acetic acid ethyl ester or isobutyric acid ethyl ester.

In an aspect of the present invention for manufacturing alkali metal salt(s) of 1,2-benzisoxazole-3-methanesulfonic acid, the inert solvent is dichloromethane, chloroform, or 1,2-dichroloethane.

Another aspect of the present invention relates to a one-pot method of manufacturing 1,2-benzisoxazole-3-methanesulfonamide, which comprises:

(a) providing or making a first mixture of 1,2-benzisoxazole-3-methanesulfonic acid and toluene by any of our present methods as described herein;

(b) adding aqueous alkali metal hydroxide solution to the first mixture and removing water by azeotoropic distillation to give a second mixture;

(c) adding phosphorous oxychloride to the second mixture and reacting the mixture to give a third mixture;

(d) adding ammonia to the third mixture and reacting the mixture to give a fourth mixture containing 1,2-benzisoxazole-3-methanesulfonamide; and (e) isolating the 1,2-benzisoxazole-3-methanesulfonamide.

Starting 1,2-Benzisoxazole-3-acetic acid is obtained by the method described in JP-A-53-77057, and so on.

Sulfonating 1,2-benzoisoxazole-3-acetic acid, in toluene, with chlorosulfonic acid proceeds selectively towards the desired product when conducted in the presence of the specific Lewis base.

The Lewis base used in the present invention is other than dioxane, and in particular is an ester or nitrile. This allows the reactivity of chlorosulfonic acid to be moderated while concurrently providing the additional advantage of significantly increasing the selectivity of the sulfonation reaction to the desired product. Suitable Lewis bases other than dioxane are represented by a compound selected from the group consisting of a $C_{2-5}$ saturated aliphatic mono-carboxylic acid $C_{1-4}$ alkyl ester, a benzoic acid $C_{1-4}$ alkyl ester, a $C_{1-4}$ alkyl cyanide and benzonitrile, and a preferred example is a $C_{2-5}$ saturated aliphatic mono-carboxylic acid $C_{1-4}$ alkyl ester.

"$C_{2-5}$ saturated aliphatic mono-carboxylic acid $C_{1-4}$ alkyl ester" means a $C_{1-4}$ alkyl ester of a straight or branched saturated aliphatic mono-carboxylic acid having 2-5 carbon atoms, and, for example, $C_2$ saturated aliphatic mono-carboxylic acid $C_2$ alkyl ester means ethyl acetate. In one of the preferred $C_{2-5}$ saturated aliphatic mono-carboxylic acid $C_{1-4}$ alkyl esters, the $C_{1-4}$ alkyl has a straight chain, and a more preferred example is a $C_{2-5}$ saturated aliphatic mono-carboxylic acid ethyl ester. Specific examples include ethyl acetate, ethyl propionate, ethyl butyrate, ethyl isobutyrate, ethyl valerate and ethyl pivalate, and preferred examples include ethyl acetate and ethyl isobutyrate.

Preferred examples of a benzoic acid $C_{1-4}$ alkyl ester include ethyl benzoate and propyl benzoate.

"$C_{1-4}$ alkyl cyanide" means a compound consisting of a straight or branched $C_{1-4}$ alkyl group and cyano group and specific samples include acetonitrile, ethyl cyanide, iso-propyl cyanide and tert-butyl cyanide.

An amount of toluene used in the sulfonation process of 1,2-benzisoxazole-3-acetic acid is selected from the range of 5-20 ml per 1 g of 1,2-benzisoxazole-3-acetic acid and preferred range is 8-10 ml.

An amount of chlorosulfonic acid in the sulfonation process for 1,2-benzisoxazole-3-acetic acid is selected from the range of 1.1-2.0 molar equivalent of the 1,2-benzisoxazole-3-acetic acid and a preferred range is 1.2-1.5 molar equivalent.

An inert solvent used in the present invention means a solvent that does not react with chlorosulfonic acid. A chlorinated hydrocarbon is preferred as the inert solvent for chlorosulfonic acid. Preferred chlorinated hydrocarbon solvents include dichloromethane, chloroform, and 1,2-dichloroethane, as examples.

The chlorosulfonic acid can optionally be mixed with an inert solvent. When chlorosulfonic acid mixed with an inert solvent is used, an amount of inert solvent is selected from the range of 2-3 ml per 1 g of chlorosulfonic acid.

An amount of the Lewis base in the sulfonation process of 1,2-benzisoxazole-3-acetic acid is selected from the range of 1.1-5.0 molar equivalent of the 1,2-benzisoxazole-3-acetic acid, and a preferred range is 2.0-3.5 molar equivalent.

The temperature for the step of adding chlorosulfonic acid to a mixture of the Lewis base, toluene and 1,2-benzisoxazole-3-acetic acid is selected from the range of 0-30° C. The reaction temperature after the addition step is selected from the range of 60-90° C. and preferably from the range of 70-85° C.

The term alkali metal salt includes the potassium and sodium salts, although the sodium salt may be preferred. Alkali metal hydroxide(s) includes, for example, potassium hydroxide and sodium hydroxide, although sodium hydroxide may be preferred.

In an aspect of a one-pot manufacturing method, a tertiary amine can be added in step (c). Amines include those represented by tertiary alkyl amines such as diisopropylethylamine and triethyl amine, and by other amines represented by pyridine, among others. If a tertiary amine is added, then triethylamine is preferred. The reaction temperature is selected from the range of 70-85° C. The tertiary amine can be added to a mixture of an intermediate and toluene before adding phosphorus oxychloride as a chlorinating agent. In the case of triethylamine, an amount is preferably selected from the range of 0.1 to 0.2 g per 1 g of chlorosulfonic acid.

In an aspect of the one-pot manufacturing method, phosphorus oxychloride is the preferred chlorinating agent. In principle $SOCl_2$/DMF may also be an effective chlorinating agent herein.

In an aspect of the one-pot manufacturing method, the ammonia used in step (d) is preferably ammonia gas, and the reaction temperature is selected from the range of 30-60° C.

In an aspect of the one-pot manufacturing method, the isolation of 1,2-benzisoxazole-3-methane-sulfonamide performed in step (e) can be accomplished in the usual manner such as, for example, in an isolating step that comprises a step of adding water to the reaction mixture, a step of crystallizing from the solvent of toluene and water, and a step of collecting the crystals such as by filtration.

The complete disclosure of U.S. Pat. No. 7,081,539B2, titled a one-pot method for the preparation of 1,2-benzisoxazole-3-methanesulfonamide, is incorporated herein by reference.

1,2-Benzisoxazole-3-methanesulfonamide manufactured by the method of present invention can be additionally purified by various methods, including extraction, column chromatography, high or low pressure chromatography, recrystallization, and slurrying, among other processes. For instance, zonisamide can be purified further by recrystallization and, optionally, in combination with azeotropic distillation. Suitable solvents for recrystalization include, for example, aqueous ethanol and aqueous iso-propyl alcohol, among others, and among these, aqueous iso-propyl alcohol is preferred, and 45-55% aqueous iso-propyl alcohol is more preferred. By way of example, a 55% aqueous $C_{2-4}$ alcohol means a mixture of 55 volume % of water and 45 volume % of $C_{2-4}$ alcohol. During the recrystallzation process, azeotropic distillation such as described in U.S. Pat. No. 6,900,333 can be performed, whereby the resultant crystals of 1,2-benzisoxazole-3-methane-sulfonamide (zonisamide) can satisfy ICH regulations concerning limits on the amount of the residual solvent, such as toluene, 1,2-dichloroethane, and so on.

EXAMPLES

The present invention is illustrated in more detail by the following examples, but the present invention is not limited thereto. The content of starting material and product, and purity of the product were measured by high performance liquid chromatography.

Room temperature usually means less than about 40° C. and in general it connotes a temperature that is in the range of 5-40° C. The room temperature in the Examples, for instance as in Examples 1, 10 and 14, refers to the temperature in a temperature controlled room, which may be regarded as about 25-27° C.

Example 1

To a mixture of 1,2-benzisoxazole-3-acetic acid (1.77 g), ethyl isobutyrate (3.48 g) and toluene (15 ml) was added dropwise chlorosulfonic acid (1.40 g) with stirring at room temperature and the resulting mixture was heated with stirring at 80° C. for 2 hours. It was confirmed that there were 70%, 21% and 8% of 1,2-benzisoxazole-3-methane sulfonic acid, starting material and a by-product, respectively, in the reaction solution. Water was added to the reaction mixture and the mixture was extracted with aqueous layer. The aqueous layer was adjusted with 25% aqueous sodium hydroxide to pH 10 and concentrated under reduced pressure. To the residue was added water until total weight became approximately 7 g and the mixture was cooled in an ice water bath. The precipitated crystals were collected by filtration and dried at room temperature to give 1.23 g of sodium 1,2-benzisoxazole-3-methanesulfonate (purity of 99%).

Examples 2-9

1,2-Benzisoxazole-3-acetic acid (1.77 g) was treated in a similar manner in Example 1 to give the following results in Table 1.

dichloromethane (5 ml) with stirring at room temperature and the resulting mixture was heated with stirring at 70° C. for 2 hours. It was confirmed that 84%, 5% and 7% of 1,2-benzisoxazole-3-methane sulfonic acid, starting material and a by-product respectively, were present in the reaction solution. Water was added to the reaction mixture and the mixture was extracted with aqueous layer. The aqueous layer was adjusted with 25% aqueous sodium hydroxide to pH. 10 and concentrated under reduced pressure. To the residue was added water until the total weight

TABLE 1

| Example | Toluene | Chlorosulfonic acid | Lewis base | Contents in a reaction mixture | | | Yield (Purity) |
| | | | | Desired compound | Starting material | By-product[1] | |
| --- | --- | --- | --- | --- | --- | --- | --- |
| 1 | 15 ml | 1.40 g | Ethyl isobutyrate 3.48 g | 70% | 21% | 8% | 1.23 g (99%) |
| 2 | 15 ml | 1.40 g | Ethyl acetate 2.64 g | 67% | 26% | 6% | 1.48 g (90%) |
| 3 | 15 ml | 1.75 g | Ethyl acetate 2.64 g | 64% | 23% | 12% | 1.75 g (94%) |
| 4 | 15 ml | 1.40 g | Ethyl propionate 3.06 g | 63% | 28% | 7% | 1.29 g (93%) |
| 5 | 15 ml | 1.40 g | Methyl pivalate 3.48 g | 60% | 25% | 8% | 1.21 g (93%) |
| 6 | 15 ml | 1.40 g | Ethyl pivalate 3.91 g | 62% | 29% | 9% | — |
| 7 | 15 ml | 1.40 g | Ethyl benzoate 4.51 g | 63% | 28% | 9% | 1.29 g (91%) |
| 8 | 18 ml | 1.40 g | Benzonitrile 1.55 g | 53% | 23% | 8% | 1.25 g (91%) |
| 9 | 18 ml | 1.40 g | tert-Butyl cyanide 1.25 g | 66% | 23% | 8% | 1.12 g (92%) |

[1] A reaction product with toluene and chlorosulfonic acid.

Reference Examples 1-5

1,2-Benzisoxazole-3-acetic acid (1.77 grams) was treated in a similar manner in Example 1 to give the following results in Table 2.

became approximately 7 g and the mixture was cooled in an ice water bath. The precipitated crystals were collected by filtration and dried at room temperature to give 2.38 9 of sodium 1,2-benzisoxazole-3-methane sulfonate (purity of 96%).

TABLE 2

| Reference Example | Toluene | Chlorosulfonic acid | Lewis base | Contents in a reaction mixture | | | Yield (Purity) |
| | | | | Desired compound | Starting material | By-product[1] | |
| --- | --- | --- | --- | --- | --- | --- | --- |
| 1 | 18 ml | 1.40 g | 1,4-Dioxane 1.32 g | 81% | 12% | 5% | 1.59 g (92%) |
| 2 | 15 ml | 1.40 g | 1,2-Diethoxyethane 3.54 g | 51% | 24% | 5%, 18%[2] | — |
| 3 | 18 ml | 1.40 g | DMF 1.10 g | 3% | 88% | 9% | — |
| 4 | 36 ml | 2.10 g | 1-methyl-2-pyrrolidone 2.23 g | 4% | 80% | 13% | — |
| 5 | 18 ml | 2.33 g | none | 25% | 29% | 44% | — |

[1] A reaction product of toluene with chlorosulfonic acid.
[2] By-products other than a reaction product of toluene with chlorosulfonic acid.

Example 10

To a mixture of 1,2-benzisoxazole-3-acetic acid (1.77 g), ethyl acetate (2.64 g) and toluene (15 ml) was added dropwise a solution of chlorosulfonic acid (1.75 g) in Examples 11-13

1,2-Benzisoxazole-3-acetic acid (1.77 grams) was treated in a similar manner in Example 10 to give the following results in Table 3.

TABLE 3

| Example | Toluene | Chlorosulfonic acid | Solvent | Lewis base | Desired compound | Starting material | By-product[1] | Yield (Purity) |
|---|---|---|---|---|---|---|---|---|
| 10 | 15 ml | 1.75 g | Dichloroethane 5 ml | Ethyl acetate 2.64 g | 84% | 5% | 7% | 2.38 g (96%) |
| 11 | 15 ml | 1.75 g | Chloroform 5 ml | Ethyl acetate 2.64 g | 86% | 4% | 6% | 2.41 g (96%) |
| 12 | 15 ml | 1.75 g | 1,2-Dichloroethane 5 ml | Acetonitrile 1.23 g | 78% | 5% | 9% | — |
| 13 | 15 ml | 2.10 g | 1,2-Dichloroethane 5 ml | tert-Butyl cyanide 2.49 g | 74% | 11% | 12% | — |

[1]A reaction product of toluene with chlorosulfonic acid.

Example 14

1) To a mixture of 1,2-benzisoxazole-3-acetic acid (10.6 g), ethyl acetate (15.9 g) and toluene (90 ml) was added dropwise a solution of chlorosulfonic acid (10.5 g) in 1,2-dichloroethane (30 ml) for 15 minutes with stirring at room temperature and the mixture was kept stirring at room temperature for 20 minutes. After stirring at 70-80° C. for 2 hours, ethyl acetate was removed by distillation and the residue was adjusted with 25% aqueous sodium hydroxide to pH 10. An operation, which consisted of adding toluene (60 ml) to the mixture and concentrating the mixture under reduced pressure, was repeated three times to remove water. Toluene (70 ml), triethylamine (1.3 g) and phosphorous oxychloride (9.2 g) were added to the residue and the mixture was stirred at 77-80° C. for 6 hours. After cooling, to the reaction mixture was added toluene (50 ml), and saturated with ammonia gas while the reaction temperature was kept at 30-60° C. The reaction mixture was concentrated, and water (100 ml) and toluene (15 ml) was added thereto. The mixture was stirred, and the precipitated crystals were collected by filtration, and washed with water to give crude crystals of 1,2-benzisoxazole-3-methanesulfonamide. The purity of the crude crystals was 96.5%.

2) The above crude crystals were recrystallized from a 50% aqueous isopropanol (140 ml) to give 1,2-benzisoxazole-3-methanesulfonamide (9.7 g) having a purity of 99.8%. This crystals were recrystallized from a 50% aqueous isopropanol (60 ml) again, and dried at room temperature to give 1,2-benzisoxazole-3-methanesulfonamide (6.7 g) having a purity of 100%.

INDUSTRIAL APPLICABILITY

Toluene is usually not suitable as the solvent for the sulfonation reaction because toluene easily reacts with chlorosulfonic acid; however as described above, in the presence of a particular Lewis base (esters or nitriles), we found chlorosulfonic acid reacts selectively with 1,2-benzisoxazole-3-acetic acid even in toluene to the desired product, and does so without requiring the use of dioxane. An aspect of the present invention provides an effective one-pot manufacturing process for the preparation of 1,2-benzisoxazole-3-methanesulfonamide in toluene using 1,2-benzisoxazole-3-acetic acid as a starting material, without having to isolate intermediates.

It is contemplated that various modifications of the present invention will be apparent to those skilled in the art without departing from the scope and spirit of our invention. The complete disclosure of each patent, patent publication and literature reference cited herein is incorporated by reference.

What is claimed is:

1. A one-pot method of manufacturing 1,2-benzisoxazole-3-methanesulfonamide, which comprises:
   (a) providing a first mixture of 1,2-benzisoxazole-3-methanesulfonic acid and toluene by a method, which comprises: adding chlorosulfonic acid, optionally mixed with an inert solvent, to a mixture of 1,2-benzisoxazole-3-acetic acid, toluene and a Lewis base selected from the group consisting of a $C_{2-5}$ saturated aliphatic mono-carboxylic acid $C_{1-4}$ alkyl ester, a benzoic acid $C_{1-4}$ alkyl ester, a $C_{1-4}$ alkyl cyanide and benzonitrile; and heating the mixture;
   (b) adding aqueous alkali metal hydroxide solution to the first mixture and removing water by azeotropic distillation to give a second mixture;
   (c) adding phosphorous oxychloride to the second mixture and reacting the mixture to give a third mixture;
   (d) adding ammonia to the third mixture and reacting the mixture to give a fourth mixture containing 1,2-benzisoxazole-3-methanesulfonamide; and
   (e) isolating the 1,2-benzisoxazole-3-methanesulfonamide.

2. The method according to claim 1, wherein the Lewis base is a $C_{2-5}$ saturated aliphatic mono-carboxylic acid $C_{1-4}$ alkyl ester.

3. The method according to claim 1, wherein the Lewis base is a $C_{2-5}$ saturated aliphatic mono-carboxylic acid ethyl ester.

4. The method according to claim 1, wherein the Lewis base is ethyl acetate or isobutyric acid ethyl ester.

5. The method according to claim 1, wherein the inert solvent is dichloromethane, chloroform, or 1,2-dichloroethane.

6. The method according to claim 1, wherein the aqueous alkali metal hydroxide solution is aqueous sodium hydroxide solution.

7. The method according to claim 1, wherein the ammonia is ammonia gas.

8. The method according to claim 1, wherein a tertiary amine is added to the second mixture in step (c).

* * * * *